United States Patent
Lashinski

(10) Patent No.: US 6,579,305 B1
(45) Date of Patent: Jun. 17, 2003

(54) METHOD AND APPARATUS FOR DELIVERY DEPLOYMENT AND RETRIEVAL OF A STENT COMPRISING SHAPE-MEMORY MATERIAL

(75) Inventor: Robert Lashinski, Windsor, CA (US)

(73) Assignee: Medtronic AVE, Inc., Santa Rosa, CA (US)

( * ) Notice: Subject to any disclaimer, the term of this patent is extended or adjusted under 35 U.S.C. 154(b) by 0 days.

(21) Appl. No.: 08/568,543

(22) Filed: Dec. 7, 1995

(51) Int. Cl.⁷ .......................... A61F 2/06; A61M 29/00
(52) U.S. Cl. .................. 623/1.11; 623/1.19; 606/192; 606/194
(58) Field of Search ................ 604/96, 102; 623/1, 623/11, 12, 1.11, 1.19; 606/108, 191, 194, 195, 198, 192

(56) References Cited

U.S. PATENT DOCUMENTS

| 4,503,569 A | | 3/1985 | Dotter |
| 4,512,338 A | | 4/1985 | Balko et al. |
| 4,584,998 A | * | 4/1986 | McGrail ..................... 604/102 |
| 4,646,742 A | * | 3/1987 | Packard et al. ............. 604/102 |
| 4,955,895 A | * | 9/1990 | Sugiyama et al. .......... 604/102 |
| 5,147,385 A | | 9/1992 | Beck et al. |
| 5,163,952 A | | 11/1992 | Froix |
| 5,242,451 A | * | 9/1993 | Harada et al. ............... 623/12 |
| 5,466,242 A | * | 11/1995 | Mori ........................... 606/198 |
| 5,599,307 A | * | 2/1997 | Bacher et al. .............. 604/101 |
| 5,603,722 A | * | 2/1997 | Phan et al. .................. 606/198 |
| 5,667,522 A | | 9/1997 | Flomenblit et al. |
| 5,827,322 A | * | 10/1998 | Williams ..................... 606/198 |
| 5,947,977 A | * | 9/1999 | Slepian et al. ............. 606/108 |

FOREIGN PATENT DOCUMENTS

| EP | 0 626 153 A1 | 11/1994 |
| EP | 0 666 065 A1 | 8/1995 |

OTHER PUBLICATIONS

Sugita, et al., "Nonsurgical Implantation of a Vascular Ring Prosthesis using Thermal Shape Memory Ti/Ni Alloy (Nitinol Wire)," *Trans Am Soc Artif Intern Organs*, Vo. XXXII.

* cited by examiner

*Primary Examiner*—Corrine McDermott
*Assistant Examiner*—Alvin Stewart

(57) ABSTRACT

A delivery, deployment and retrieval device for a stent made from a phase-change material includes a balloon catheter modified to allow the stent to be secured on the outside of the balloon without the need for a sheath. A temperature-controlled fluid to effect a phase change to expand the stent is injected through an inflation lumen to maintain the selected temperature and to inflate the balloon. The balloon maintains intimate physical and thermal contact with the stent during deployment. One or more exit apertures are provided for the fluid to escape from the inflation lumen and enhance the phase change by bathing the stent with the fluid.

2 Claims, 4 Drawing Sheets

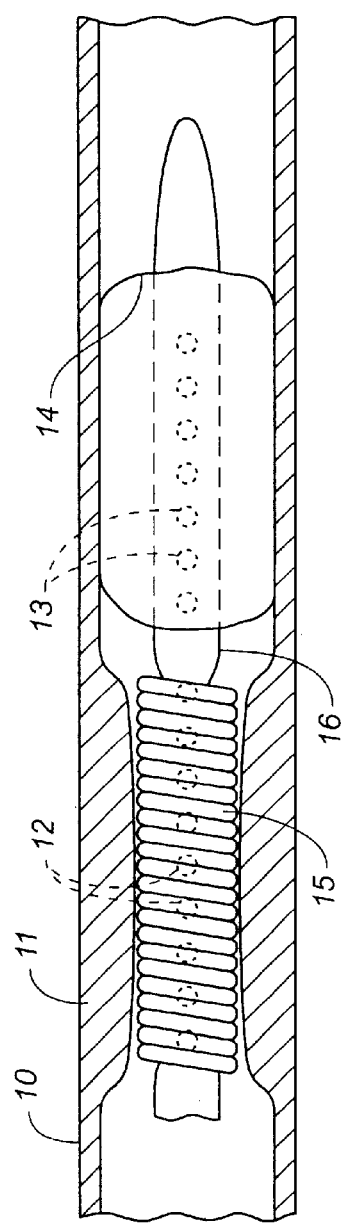
FIG._1
(PRIOR ART)
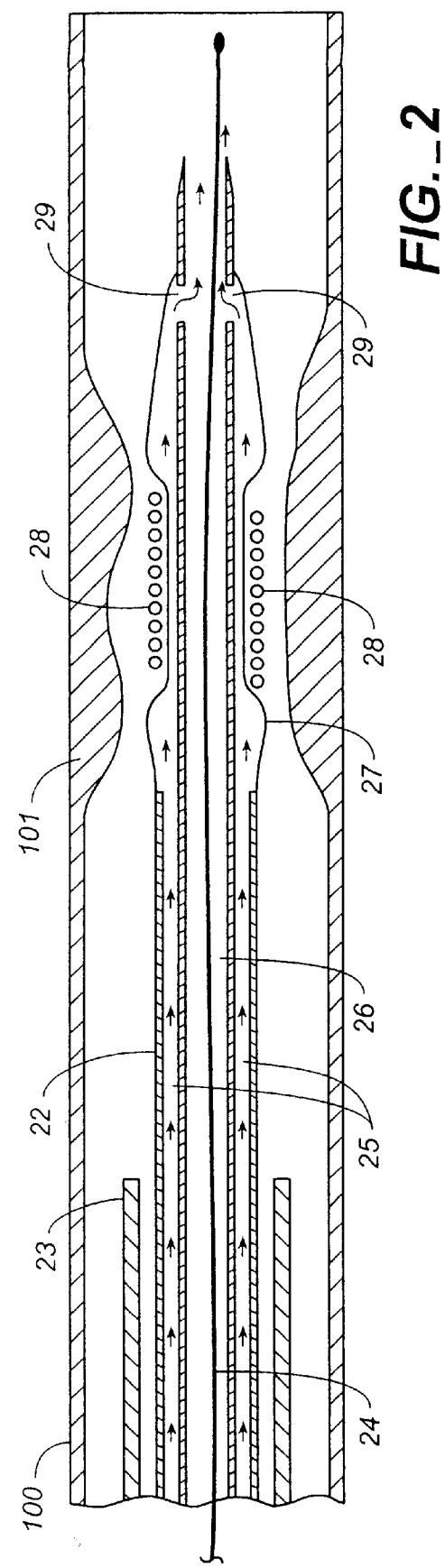
FIG._2

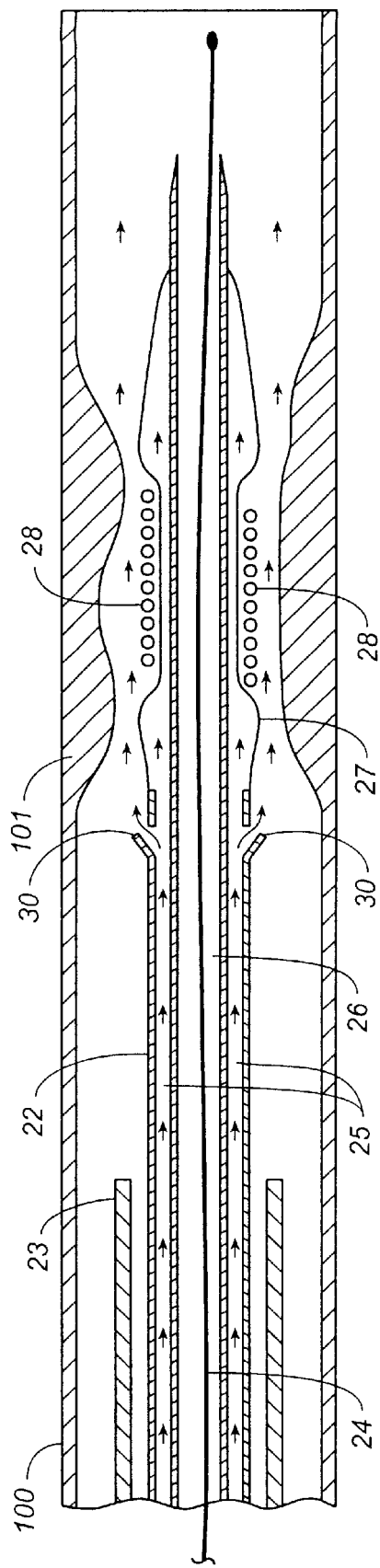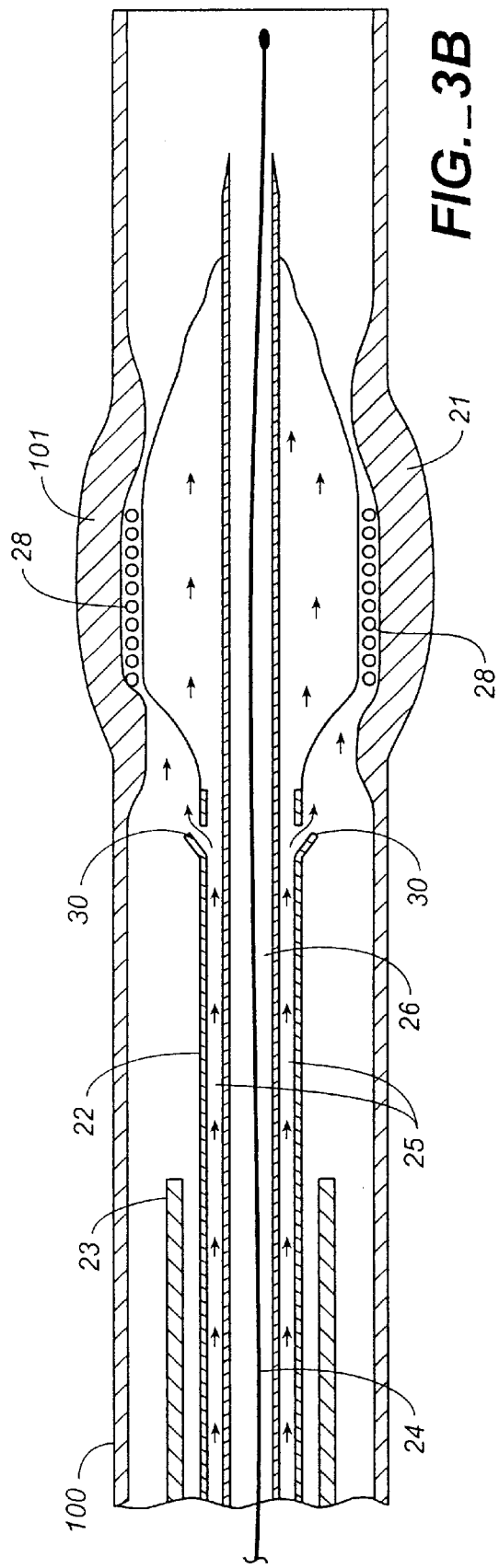

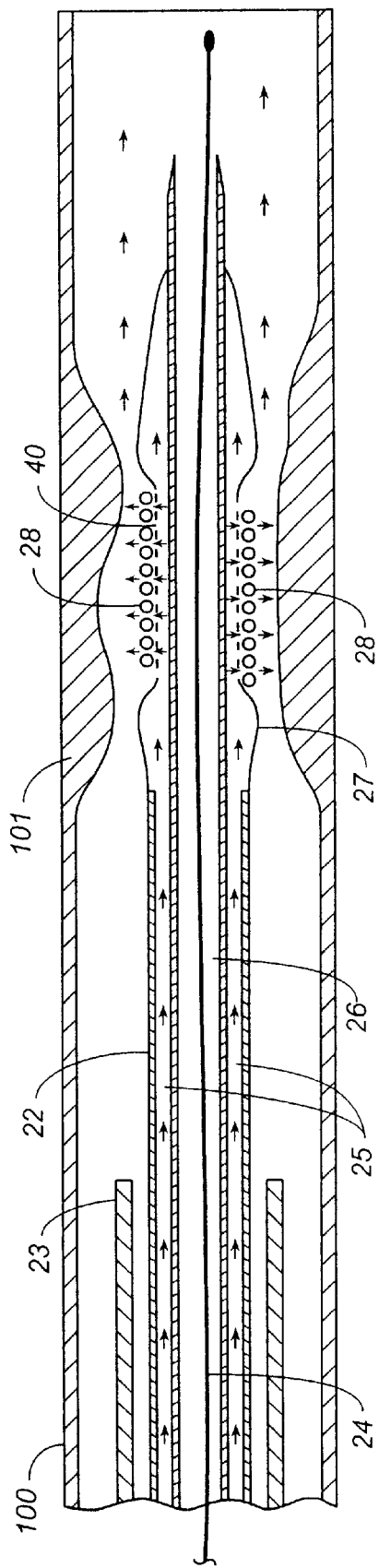
FIG._4
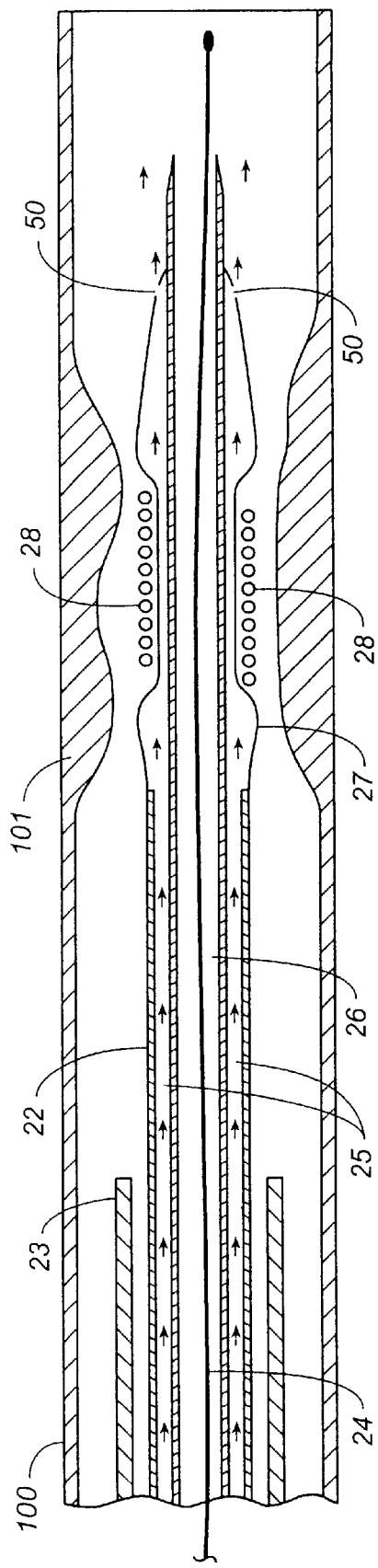
FIG._5

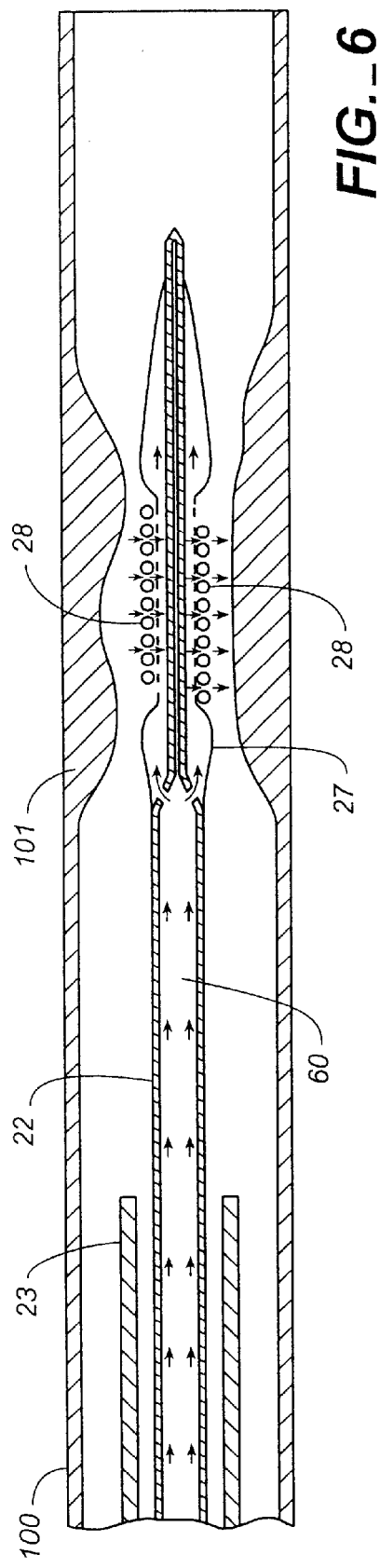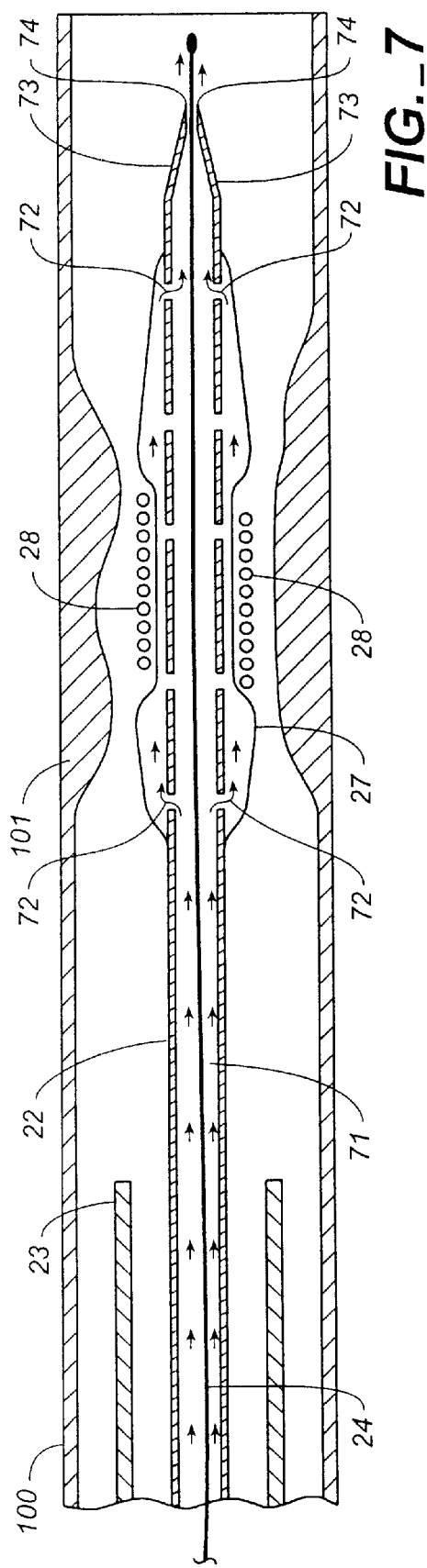

METHOD AND APPARATUS FOR DELIVERY DEPLOYMENT AND RETRIEVAL OF A STENT COMPRISING SHAPE-MEMORY MATERIAL

FIELD OF THE INVENTION

This invention relates to methods and apparatus for delivering, deploying and retrieving medical endoprostheses, commonly referred to as "stents". More specifically, the invention relates to delivering a stent composed of shape-memory material on a balloon catheter without using an outer protective sheath, and deploying the stent by introducing temperature-controlled fluid through the balloon catheter to induce a shape change in the shape-memory material, the fluid causing the balloon to expand along with the stent thereby enhancing control over placement of the stent and enabling retrieval of the stent when necessary.

BACKGROUND OF THE INVENTION

Stents are known in the prior art for maintaining the patency of a diseased or weakened vessel or other passageway. Stents have been implanted, for example, in passageways in the urinary tract system and in the coronary arteries of the endovascular system. Such mechanical prosthetic devices are typically inserted into the vessel, positioned across an affected area and then expanded, or allowed to self-expand, to keep the vessel or passageway open. Effectively, the stent overcomes the natural tendency of the weakened area to close. Stents used in the vascular system are generally implanted transluminally during or following percutaneous transluminal coronary angioplasty (angioplasty or PCTA).

A number of vascular stents have been proposed, including self-expanding stents and expandable stents. Self-expanding stents may be mechanically compressed springs which expand when released, and/or they may be constructed from shape-memory materials including shape-memory polymers and metals such as nickel-titanium ("Nitinol") alloys and the like, which have shape-memory characteristics.

In a manner known in the art, a stent formed of shape-memory alloy such as nickel-titanium is formed into a desired expanded configuration and then heated until the metal crystals assume their high-temperature structure known as the beta phase, parent phase or austenite. The stent is then cooled so that the crystals transition to a martensite crystal structure, generally with no change in shape. The material is then formed into a reduced diameter configuration for implantation.

When the temperature of the stent is later raised so that the crystal structure transitions to the parent phase, the shape of the stent returns to the desired expanded configuration. Typically, a material having a phase-change transition temperature in excess of 125° F. is chosen to prevent premature expansion of the stent upon exposure to human body temperature (98.6° F.). However, materials with lower phase-change transition temperatures may be used, provided the stent is insulated from the human body temperature prior to reaching the location for deployment.

Dotter U.S. Pat. No. 4,503,569 describes a stent comprising a helically wound coil of shape-memory alloy that is placed over the outer wall of a guide catheter. The stent and guide catheter are carried within an outer sheath. At the delivery site, the outer sheath is withdrawn. A hot saline solution is then injected through the inner guide catheter and flows out of the catheter through apertures, so that the fluid bathes the stent and causes it to expand. The patent describes that a balloon may be positioned on one or both sides of the stent to reduce thermodilution of the saline solution and enhance the phase change.

Balko et al. U.S. Pat. No. 4,512,338 which discloses a Nitinol wire stent in the form of a coil which is delivered to the desired site while housed inside of an insulating sheath. When the insulating sheath is withdrawn, the surrounding body temperature causes the stent to expand.

Froix U.S. Pat. No. 5,163,952 discloses shape-memory-polymer tubular and coil stents having an elastic memory which causes them to expand to a predetermined diameter upon exposure to particular conditions. Shape-memory polymer stents are initially formed having the desired expanded diameter. The stents are then physically stretched at elevated temperature causing them to assume a reduced diameter. While under tension, the stents are cooled to below the glass transition phase of the plastic. The stent then remains in the stretched and reduced-diameter configuration until after the stent is raised to above the glass transition temperature at the site desired to be treated. Depending upon the polymer selected and process of manufacture, stents can be formed to expand by different degrees and upon exposure to various conditions including various temperatures.

Various methods have been used to induce the temperature change required to effect the shape-memory characteristic, including intervascular electrical resistive heating elements, R.F., and temperature-controlled fluid boluses injected through a guide catheter around the delivery catheter.

A drawback of previously known delivery systems for shape-memory material stents is the use of a protective sheath to prevent premature expansion at body temperatures and to enhance delivery through the tortuous vessels of the vascular system. Such sheaths increase the cross-sectional profile of the delivery system, necessitating use of a delivery catheter with a larger diameter. The large diameter of the delivery catheter may in turn increase the risk of complications at the patient access site.

The increased cross-sectional profile of the delivery system also detracts from the ability of the device to navigate through tortuous vessels or passageways. The increased cross-sectional profile of the delivery system may make it impossible to deliver a phase-change material stent to the area desired to be treated and may decrease the ability to deliver sufficient contrast material through the guide catheter for enabling precise positioning.

Another drawback of self-expanding stents, both coiled spring stents and phase-change stents, is the inability to control expansion of the stent once the stent loses contact with the guide catheter. In particular, as the stent expands, or is pushed out of a catheter for self-expansion, it moves radially out of contact with the delivery device. Because there no longer is contact between the stent and the delivery device, there is no mechanism to control positioning of the stent location during this critical phase of deployment. Consequently, the stent may move away from the desired site.

Yet another problem is encountered when elevated (or reduced) temperatures are required to cause the phase change in the stent material. For example, in the system described in the Dotter patent, the fluid flowing through the catheter exchanges heat with the vessel wall, and as the fluid flows out of the catheter it is diluted by the blood or other fluids contained in the vessel. Thus, it may be necessary to flush large volumes of liquid through the guide catheter to maintain the required temperature environment around the stent to effect deployment. The injection of such large volumes of hot or cold fluid into the vessel may be injurious or hazardous to the vessel and the tissues through which it passes.

It would therefore be desirable to provide methods and apparatus for delivering a shape-memory material stent to an affected area of a vessel without using a sheath.

It would further be desirable to provide methods and apparatus for effecting the phase change of the stent without perfusing large quantities of fluid into the vessel to be treated.

It would still further be desirable to provide methods and apparatus for maintaining control over the positioning of a phase-change stent during deployment.

SUMMARY OF THE INVENTION

It is an object of this invention to provide methods and apparatus for delivering a phase-change stent to an affected area of a vessel without using a sheath.

It is a further an object of this invention to provide methods and apparatus for effecting the phase change of the stent without perfusing large quantities of fluid into the vessel to be treated.

It is still further an object of this invention to provide methods and apparatus for maintaining control over the positioning of a phase-change stent during deployment.

These and other objects of the invention are accomplished in accordance with the principles of the invention by providing a phase-change stent crimped or encapsulated onto the balloon of a balloon catheter having perfusion apertures communicating from the inflation lumen to the exterior of the catheter to enable a temperature-controlled fluid to be used both to pressurize the balloon and induce expansion of the stent. Some of the intended uses for a delivery system in accordance with the present invention include PTCA type stenting, PTA type stenting, graft support, graft delivery, INR use, GI tract use, drug delivery, and biliary stenting.

BRIEF DESCRIPTION OF THE DRAWINGS

FIG. 1 is an elevational view of a distal end of a previously known stent deployment catheter.

FIG. 2 is a cross-sectional view of a distal end of a stent deployment system constructed in accordance with the present invention.

FIGS. 3A and 3B show cross-sectional views, respectively, prior to and during deployment, of the distal end of a stent deployment system according to the present invention.

FIG. 4 is a cross-sectional view of a distal end of an alternative embodiment of a stent deployment system according to the present invention.

FIG. 5 is a cross-sectional view of a distal end of another alternative embodiment of a stent deployment system according to the present invention.

FIG. 6 is a cross-sectional view of a distal end of a single-lumen embodiment of a stent deployment system according to the present invention.

FIG. 7 is a cross-sectional view of the distal end of an alternative single-lumen embodiment of a stent deployment system according to the present invention.

DETAILED DESCRIPTION OF PREFERRED EMBODIMENTS

The present invention relates generally to methods and apparatus for deploying stents made of shape-memory material. In particular, according to the present invention, a phase-change stent may be crimped or encapsulated onto the balloon of a balloon catheter. Encapsulation of the stent may be accomplished as described in U.S. patent application Ser. No. 08/451,270, filed on May 30, 1995, which is hereby incorporated by reference.

In accordance with the present invention, a stent delivery system is provided including a balloon catheter having an inflation lumen in fluid communication with one or more perfusion apertures. Temperature-controlled fluid introduced into the inflation lumen serves both to pressurize and expand the balloon and also escape via the perfusion apertures to bathe the stent. This arrangement allows for the temperature of the stent to be controlled by the exiting fluid, while the inflating balloon maintains contact with the expanding stent. The balloon therefore assists in controlling the location of the stent during deployment and may also assist in its expansion in a conventional manner.

Referring to FIG. 1, an illustrative prior art stent deployment system, such as disclosed in the above-mentioned Dotter patent, is described. Coil stent 15 is shown compressed onto guide catheter 16. Guide catheter 16 has perfusion apertures 12 which enable heated saline to be directed over the stent to effect the phase change and expansion. During and after this deployment, coil stent 15 expands out of contact with guide catheter 16. Holes 13 allow the heated saline to inflate distally-located balloon 14 to reduce thermodilution of the heated saline from the vicinity of the stent.

Referring now to FIG. 2, an illustrative embodiment of a stent delivery system of the present invention is described. Stent 28 illustratively forms a coil of shape-memory material, for example, Nitinol, positioned over balloon 27 of balloon catheter 22 in a stent engagement region. Shape-memory materials can also be used to form other stent configurations, such as tubular stents, without departing from the present invention. Balloon catheter 22 may be formed of conventional catheter materials and includes two lumens, central lumen 26 for receiving guidewire 24 and inflation lumen 25 for supplying temperature-controlled fluid to balloon 27.

Balloon catheter 22 is delivered over guidewire 24, through guide catheter 23, to stenosis 101 in vessel 100 using conventional catheterization techniques. When located at the site of stenosis 101, temperature-controlled fluid is introduced through inflation lumen 25 to balloon 27 as shown by the arrows in FIG. 2. This fluid, which may be heated saline, pressurizes balloon 27 pushing it into intimate physical and thermal contact with stent 28. Stent 28, under the influence of the pressure and temperature from balloon 27, expands to its deployed form. Balloon 27 and stent 28 therefore remain in intimate contact at all times during this deployment, enabling accurate placement of stent 28.

As seen in FIG. 2, a plurality of apertures 29 are formed between the interior of balloon 27 and central lumen 26 distally of the stent location. These apertures are dimensioned to allow controlled leakage of the temperature-controlled fluid into central lumen 26, and thence into vessel 100, to maintain the temperature of the fluid in the balloon. Apertures 29 have sufficient size, for example, about 10 mils, and number that balloon 27 is sufficiently pressurized to be maintained in intimate contact with stent 28 during deployment.

With respect to FIGS. 3A and 3B, an alternative embodiment of the stent delivery system of the present invention is described. Elements common with FIG. 2 are indicated by like reference numerals in FIGS. 3A and 3B. In FIG. 3A, stent 28 is compressed onto balloon 27 of balloon catheter 22. Balloon catheter 22 includes perfusion jets 30 located proximally of the stent position, by which temperature-controlled fluid may exit balloon catheter 22 and bathe the stent.

Perfusion jets 30 direct temperature-controlled fluid from inflation lumen 25 over stent 28. This provides a second means effecting the phase change in stent 28 in addition to heat exchange with balloon 27, as in the embodiment of FIG. 2. Perfusion jets 30 also may be used as an alternative to, or in addition to, distally-located apertures 29 described with respect to the embodiment of FIG. 2. Perfusion jets 30 are provided in sufficient number and size, for example, having a diameter of 10 mils, to enable balloon 27 to be adequately pressurized.

FIG. 3B illustrates operation of the delivery system and stent 28 during deployment. As seen in FIG. 3B, balloon 27 maintains intimate contact with stent 28 during deployment, thereby providing both temperature control and accurate placement of stent 28. Balloon 27 may additionally assist in the expansion of the stent by the application of radial expansion pressure to the stent.

Referring now to FIG. 4, another alternative embodiment of the present invention is described in which balloon 27 has a plurality of perfusion pores 40 located in the stent engagement region of the balloon. Perfusion pores 40 permit seepage of temperature-controlled fluid through the wall of balloon 27 directly onto stent 28. Perfusion pores 40 may be macroscopic or microscopic apertures, depending upon the choice of material for the balloon, and are preferably evenly distributed over the area within which the stent is located. As with the embodiments of FIGS. 2 and 3, the size and number of perfusion pores 40 is selected so that adequate pressure may be maintained in balloon 27 during deployment of stent 28.

FIG. 5 illustrates yet another alternative embodiment of the stent delivery system of the present invention. In the embodiment of FIG. 5, balloon catheter 22 includes external apertures 50 located distally of the stent location. Apertures 50 may be provided through balloon 27 or may be in the form of a partial seal between balloon 27 and central lumen 26. In this embodiment, temperature-controlled fluid leaks out of the balloon in a controlled manner downstream of stent 28. The fluid in the balloon is continually replenished through inflation lumen 25, thus maintaining the pressure and temperature of the fluid in balloon 27.

With respect to FIG. 6, a single lumen embodiment of the present invention is described. As seen in FIG. 6, balloon catheter 22 includes a single lumen 60. The absence of a guidewire and central lumen 26 allows for a significant reduction in the diameter of the stent delivery system. However, because balloon catheter 22 does not permit use of a guidewire, the catheter must itself be steerable. This can be acheived using the conventional technology of fixed-wire stents.

Balloon catheter 22 of FIG. 6 includes perfusion pores 40 in balloon 27 in the stent engagement region. Perfusion pores 40 allow temperature-controlled fluid to bathe stent 28, as shown by the arrows in FIG. 6. Like the previously described embodiments, balloon 27 is maintained in intimate physical and thermal contact with stent 28 during deployment, thus assisting deployment and positioning of the stent.

Referring now to FIG. 7, an alternative embodiment of a single lumen delivery system is described. Balloon catheter 22 includes inflation lumen 71 that communicates with the interior of balloon 27 via apertures 72. Inflation lumen 71 is also adapted to receive guidewire 24. A taper 73 is provided in the distal end of the catheter so that inflation lumen 71 is only slightly larger than guidewire 24. The small remaining gap between the guidewire and the exterior of inflation lumen 71 forms aperture 74. Aperture 74 permits escape of temperature-controlled fluid from the balloon as shown by the arrows.

Temperature-controlled fluid flows through apertures 72 into balloon 27, as shown by the arrows in FIG. 7, to control the balloon temperature and pressurize the balloon during stent deployment. Apertures 72 are of sufficient number and size so as to ensure adequate pressurization of the balloon to maintain contact with the stent and also adequate flow through the balloon to maintain the temperature of the fluid.

Further in accordance with the above-described methods and apparatus, a deployed stent comprising a two-way shape-memory material or a mechanically expanded stent having a shape memory of a reduced diameter may be retrieved using the above-described apparatus. A stent comprising a two-way shape-memory material changes from its contracted configuration to its expanded configuration, and vice-versa, when it experiences a phase change.

The retrieval process begins by positioning the deployment device inside of the lumen of an expanded stent. A fluid at a temperature selected to cause the phase-change material of the stent to contract is then introduced to the balloon, which expands to contact the deployed stent and to place the fluid in thermal contact with the stent. As the stent changes phase, it contracts onto the balloon, and when the phase change is completed, perfusion may be halted. The balloon is then deflated and the delivery system withdrawn to retrieve the stent.

While one application for the above-described stent includes treatment of cardiovascular disease such as atherosclerosis or other forms of coronary narrowing, the present invention may also be used for treatment of narrowed vessels in other components of the vascular system, for example, the kidney, leg, carotid artery, or elsewhere in the body. As will of course be appreciated, the size of the stent and the stent delivery system, as well as their external characteristics, may need to be adjusted to compensate for the differing sizes of the vessel or passageway to be treated.

While this invention has been described in connection with illustrative preferred embodiments thereof, modifications and changes may be made thereto by those skilled in the art without departing from the spirit and scope of the invention. In particular, the location of the various apertures shown in FIGS. 2–7 are for illustrative purposes only. A typical catheter according to the present invention would have a combination of such apertures designed so as to optimize the temperature environment of the stent through the combination of contact with the balloon and direct contact with the perfusing temperature-controlled fluid. Moreover, this invention can be used for the deployment and retrieval of shape-memory stents of many different configurations. Accordingly, the scope of this invention is to be limited only by the appended claims.

What is claimed is:

1. A stent delivery system comprising:
   a catheter having a first tube and a second tube, said first tube having a proximal end, a distal end and a first lumen and said second tube disposed concentrically within said first tube, the first lumen being defined by an annulus between said first and second tubes;

a balloon sealingly connected to said first tube adjacent the distal end, the balloon defining an interior volume and having an exterior surface defining a stent engagement region, the interior volume of said balloon in communication with the first lumen; and a shape-memory alloy stent having been compressed at a temperature below a phase-change transition temperature of the stent material on said balloon in the stent engagement region of said balloon to a reduced diameter configuration, said stent having a phase-change transition temperature chosen to prevent expansion of the stent upon exposure to body temperature, such that upon pressurized introduction of a fluid having a temperature in excess of the phase-change transition temperature through the proximal end of said first lumen, the balloon is pressurized and heats said stent engagement region to cause the stent temperature to increase to undergo a phase-change transition to so cause the stent to expand to return to its austenite phase configuration, an expanded configuration which has a diameter substantially larger than said reduced diameter configuration, wherein the second tube defines a second lumen adapted for receiving a guidewire, said first tube further including a portion defining at least one aperture through the wall located proximally of said stent engagement region by which the heated fluid may exit the first tube and bathe the stent.

2. The stent delivery system as in claim 1, wherein said shape-memory alloy stent is tubular and wherein said stent having been compressed on said balloon in the stent engagement region of said balloon is done by crimping.

* * * * *